United States Patent [19]

Rao et al.

[11] Patent Number: 5,011,588
[45] Date of Patent: Apr. 30, 1991

[54] ION SELECTIVE DIP ELECTRODE ASSEMBLY

[76] Inventors: K. Jagan M. Rao; K. Savitri Rao, both of 2 Baldwin Hill Pl., Moorestown, N.J. 08052

[21] Appl. No.: 324,294

[22] Filed: Mar. 15, 1989

Related U.S. Application Data

[63] Continuation-in-part of Ser. No. 138,361, Dec. 26, 1987, abandoned, which is a continuation-in-part of Ser. No. 908,363, Sep. 17, 1986, abandoned.

[51] Int. Cl.$^5$ .............................................. G01N 27/30
[52] U.S. Cl. .................................... 204/409; 204/416; 204/418
[58] Field of Search ................ 204/409, 413, 414, 416, 204/417, 418, 435

[56] References Cited

U.S. PATENT DOCUMENTS

| | | | |
|---|---|---|---|
| 4,149,950 | 4/1979 | Potts | 204/409 |
| 4,233,136 | 11/1980 | Spaziani | 204/409 |
| 4,263,115 | 4/1981 | Kessler | 204/416 |
| 4,314,895 | 2/1982 | Spaziani | 204/417 |
| 4,486,290 | 12/1984 | Cahalan | 204/414 |
| 4,500,402 | 2/1985 | Miles | 204/242 |
| 4,519,973 | 5/1985 | Cahalan | 204/414 |
| 4,549,951 | 10/1985 | Knudson | 204/416 |
| 4,551,222 | 11/1985 | Uematsu | 204/417 |
| 4,565,665 | 1/1986 | Fogt | 204/414 |
| 4,600,495 | 7/1986 | Fogt | 204/409 |

Primary Examiner—John F. Niebling
Assistant Examiner—Ben C. Hsing
Attorney, Agent, or Firm—Donald C. Simpson

[57] ABSTRACT

A dip electrode assembly comprising as a key element a porous and a preferably microporous membrane support impregnated with a membrane matrix of an organic plastic material containing a nonvolatile solvent plasticizer and an ion-active material dissolved in the plasticizer, the plasticizer not being a solvent for the membrane support. There is also disclosed an electrode assembly involving a membrane material in which the membrane material communicates electrically directly through a metal conductor.

3 Claims, 2 Drawing Sheets

ION SELECTIVE DIP ELECTRODE ASSEMBLY

This application is a continuation-in-part of U.S. patent application Ser. No. 138,361 filed Dec. 26, 1987, which in turn is a continuation of U.S. patent application Ser. No. 908,363, filed Sept. 17, 1986, now abandoned.

This invention relates to electrochemical analytical devices and particularly to a new and improved ion-selective electrode structure used in the determination of ion (activities) concentrations, and methods for making such structures.

BACKGROUND OF INVENTION

The use of electrochemical devices for determining and measuring (activity) concentration of ions in solutions is now commonplace. In the usual form, such a device consists of a ion-selective electrode such as for instance a pH-selective glass electrode which is immersed into the solution whose ion (activity) concentration is to be measured. When the ion-selective electrode is immersed into the solution, a potential difference develops between the inner and outer layers of the membrane which is related to the ionic concentrations of the solution. Essentially, the ion-selective electrode and the solution constitute a half-cell and the developing potential is called the half-cell potential of the ion-selective electrode. To measure this half-cell potential, it is necessary to connect the ion-selective electrode and the solution to an electric measuring circuit. To do this, it is necessary to bring the solution into contact with another electrode, whereby the second electrode, also called reference electrode, should develop a constant half-cell potential which is essentially unaffected by concentration changes in the test solution. Usual practice employs a substantially reversible electrode system such as calomel electrode which is surrounded by an electrolyte such as, for instance, a saturated KCl solution, which in turn contacts the test solution. The junction between test solution and saturated KCl solution is called liquid junction. Generally one provides a constriction in the liquid path between two half cells which reduces the liquid flow between the half cells to a minimum, yet permits electrical conduction through the adjoining liquids.

Ion-selective electrodes obey the Nernst Equation:

$$E = E_0 + (RT/nF)\log a_i$$

wherein:
- E = the single electrode potential;
- $E_0$ = the reference electrode potential;
- R = the gas constant;
- T = the absolute temperature;
- n = the valence of the ion;
- F = Fraday's constant; and
- $a_i$ = the ion activity in the solution.

Any change in the activity of the measured species in solution causes a change in the measured potential which can be related to the (activity) concentration of the unknown specimen by proper calibration. Ion-selective electrodes are available for anions (e.g. $F-$, $Cl-$, $Br-$, etc) and cations (e.g. $H+$, $Na+$, $K+$ etc.) They are also available for some divalent ions like $Ca++$.

Ion-selective electrodes are classified into four broad groups:

1. Glass electrodes, e.g. $H+$, $Na+$;
2. Pressed pellet or single crystal electrodes, e.g. $F-$, $Br+$;
3. Gas sensing electrodes Ammonia, $CO_2$.
4. Liquid membrane electrodes, e.g. $K+$, $Ca++$, etc.

The present invention deals mostly with the liquid membrane electrodes. These electrodes were originally made by dissolving the active ingredient (e.g. for $K+$, Valinomycin) in an appropriate solvent and impregnating a filter paper with this solution. Ideally, the active ingredient is practically insoluble in water and the solvent selected also has minimum solubility in water. This type of electrode is clumsy to make and has a fairly short useful life. Some electrodes were made with a built-in reservoir of the "active solution". These electrodes gave a somewhat longer life but were difficult to assemble and were not popular because of the obvious drawbacks.

The next development in liquid membrane electrodes was the making of a polymeric membrane. These were made by dissolving a polymer such as polyvinylchloride (PVC) in tetrahydrofuran (THF) and then adding the active ingredient such as Valinomycin to the mixture together with a plasticizer (in this case, diethyl hexylsebacate) which is a solvent for the active ingredient. After thoroughly mixing, the mixture is evaporated in a flat container to drive out the solvent THF. This leaves a film of PVC which can be easily peeled off from the container. Ideally this film has a thickness of 6–10 mils.

Dip electrodes were made by "gluing" a small piece of this membrane to the end of an open tube and using Ag/AgCl wire with KCl filling as the internal reference electrode. This type of electrode works well, has extended life and was easy to use.

The membranes in film form were also made into flow-thru electrodes involving a fairly complicated electrode design. These flow-thru electrodes are difficult to assemble properly and, once assembled, the life of the electrode is very unpredictable. U.S. Pat. Nos. 4,233,136 and 4,314,895 describe a "flow-through", liquid membrane electrode and a method of making the electrode. The flow-through electrode comprises a tube in which a portion of the wall comprises a membrane containing a liquid phase ion exchange material for the electrode. The membrane is integrally sealed to the wall of the flow-through tube. The method of making the electrode comprising the steps of dissolving an organic plastic matrix material in a volatile solvent and then mixing a non-volatile solvent-plasticizer and an ion exchange material (in case of $K+$ it is a neutral carrier complex), which is soluble in the plasticizer, with the plastic material and the volatile solvent. The solution thus obtained is cast on a surface to form a membrane as the volatile solvent is evaporated. The membrane is attached to a tube of organic plastic material by contacting the tube with a volatile solvent common for the membrane and the tube and abutting the membrane material against the tube. As the solvent evaporates, the tube and membrane are integrally joined. In a particular embodiment, an opening is formed in the tube to receive the membrane. A mandrel is inserted within the tube and across the opening. The membrane is then formed on the mandrel contacting the tube edges at the opening and the volatile solvent in the membrane contacts the tube edges thereby resulting in the joinder of the membrane to the tube as the volatile solvent evaporates.

In a particular embodiment of the above-described flow-through electrode for detecting potassium ions, the matrix material is polyvinylchloride, the ion-exchange material is valinomycin, the non-volatile solvent comprises 2-nitro-p-cymene and the volatile solvent is a tetrahydrofuran. The membrane thickness is preferably in the range of from 8-12 mils, the polyvinylchoride matrix material comprises from 8-26%, preferably from 12-20 %, by weight of the membrane. The patentees report that an electrode assembly according to the invention supports and seals a liquid membrane integrally with the wall of the tube thereby permitting the construction of a linear flow-through liquid membrane electrode. The smooth linear flow path avoids turbulence and eddy currents as well as mechanical discontinuities which can trap portions of the liquid sample being tested and permits a more accurate, rapid and reliable response. The use of tubing allows a small diameter flow path minimizing the amount of sample required. The matrix support of the ion exchange material and the linear flow path eliminate the danger of rupturing the liquid membrane. The fabrication of the membrane to the flow-through tube is simple and convenient.

Good performance and long life of these ion-selective electrodes requires the proper plasticizer in the membrane in a fairly large quantity and, of course, a large amount of the active ingredient which is held in the membrane with the plasticizer. One of the problems associated with the flow-through electrodes described above is the limited surface area possible if the membrane is to be structurally stable. The membrane is relatively delicate compared to the tube wall. While the membrane is bonded to the tube wall, nevertheless, the size of the "interruption" in the tube wall described by the patentees must be limited to a small area into which the membrane is relatively self-supporting. If the active area of the membrane is too great, it will cease to be self-supporting and will collapse or, at the least, be subject to rupture or breaking with relatively little force. The limited size of the available active area, therefore, severely limits the amount of plasticizer that can be maintained in the membrane and, therefore, also the amount of dissolved active ingredient. As a result, many of these structurally stable electrodes of the above described type have a relatively short life under normal use conditions.

SUMMARY OF THE INVENTION

The present invention embodies a linear flow-through electrode which comprises a tube of a porous material in which the pores are impregnated with a membrane material. The membrane comprises a matrix of an organic plastic material containing an ion exchange material and a non-volatile plasticizer which is a solvent for the ion exchange materials but not for the material of the support tube. The resulting impregnated tube can be used in the same way that the membrane-containing tube of U.S. Pat. No. 4,314,895 is employed. However, the present invention also comtemplates a preferred and superior means for effecting electrode contact in which an electrode wire is placed in direct contact with the outer side of the impregnated pores of the membrane material and held in electrical contact in that position. The electrical wire is preferably wound around the impregnated tube and additional membrane material is applied over the surface of the wire and tube to form a cohesive coating of the electrode material in electrical contact with the membrane material.

This invention also contemplates a dip-type electrode using the foregoing described solid state connection and the impregnated porous tube as two elements of the dip electrode.

DETAILED DESCRIPTION OF THE DRAWINGS

Figure 1:
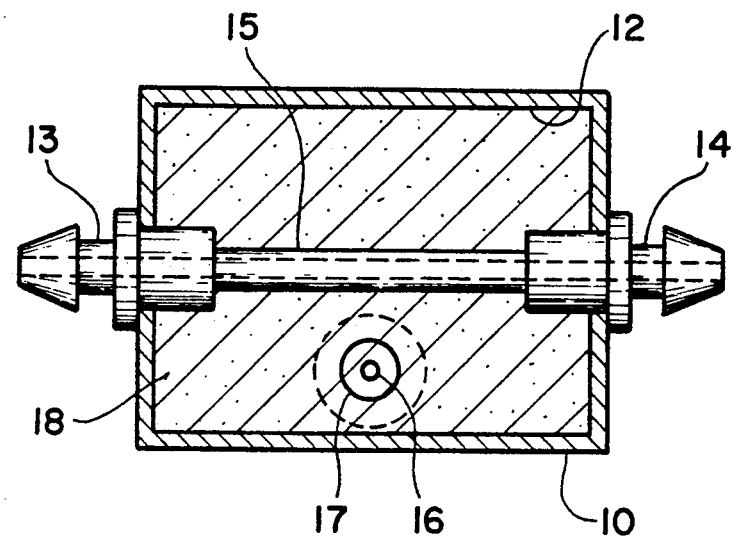
FIG. 1 is a plan view in section of an electrode assembly.
Figure 2:
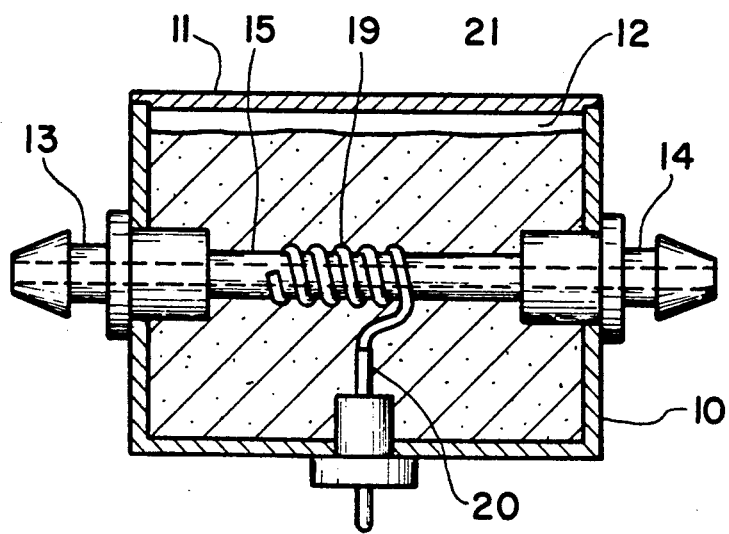
FIG. 2 is a plan view of an electrode assembly according to the invention illustrating the direct solid state connection between the electrode wire and the membrane.

Electrode assemblies according to the invention are illustrated in FIGS. 1 and 2. The asemblies comprise a housing 10 having a cover 11 defining a closed interior chamber 12. The housing and cover may be of any suitable rigid material. Axially aligned end fittings 13, 14, extend through the walls of housing 10 and define nipples to receive tubing outside of the housing. Fittings 13 and 14 have axial pores extending therethrough. A straight section of cylindrical tubing 15 extends between fittings 13, 14 and is secured therein to communicate freely through the bores of the end fittings. In the embodiment of FIG. 1, a silver-silver choloride reference electrode 16 and insulating fitting 17 supporting the electrode extend through a wall of electrode housing 10. The housing 10 contains a reference solution 18 in the form of a gel forming a salt bridge in contact with the outer surface of tube 15 and with electrode 16. Housing 10, cover 11 and fittings 13 and 14 and tube 15 are inert and electrically insulating for most embodiments. The essential difference between the electrode assembly of FIG. 1 and that illustrated U.S. Pat. No. 4,231,136 at FIGS. 1 and 2 therein, reside in the nature of the tube connecting between the end fittings and which will be discussed in greater detail subsequently herein.

The embodiment of FIG. 2 differs from the embodiment of FIG. 1 in certain very substantial ways. Electrode 16 of FIG. 1 and reference solution 18 are replaced in the embodiment of FIG. 2. Electrode 16, of FIG. 1 becomes wire 19 of FIG. 2 which is in direct contact with tube 15 and/or any coating material thereon and in direct electrical contact with electrode 20, without passing through a reference solution or without the need for the silver/silver choloride type reference electrode. Typically, wire 19 can be silver or copper or other suitable conductive metal considering the nature of the materials which it will contact. Under these circumstances, there is no necessity for the reference solution of FIG. 1. Instead, the chamber may be filled with a suitable solution of plasticizer and active ion-indicating ingredient surrounding tube 15, thereby, as it will be shown subsequently significantly extending the effective operating life of the electrode assembly of FIG. 2.

Figure 3:
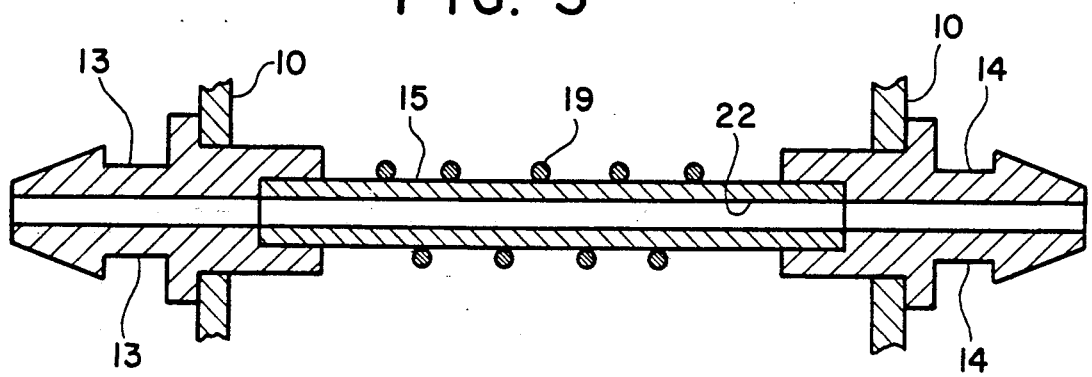
FIG. 3 is an enlarged sectional view of a portion of the electrode assembly of the invention shown in FIG. 2.

FIG. 3 illustrates in enlarged form the tube and tube connection with fittings in the embodiment of FIG. 2. Throughout this disclosure, like elements in the several figures are indicated by the same numbers. In FIG. 3 the inner portion of tube 15 is indicated at 22.

Figure 4:
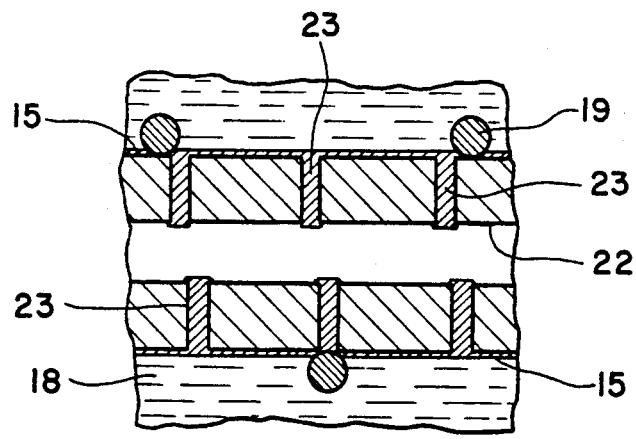
FIG. 4 is an enlarged sectional view of a portion of the electrode assembly of FIGS. 2 and 3 showing the electrical communication between electrode wire and the inside of the flow-through electrode through a pore.

As shown in an enlargement in FIG. 4, inner surface 22 communicates with the outer portion of tube 15 through pores indicated generally by the number 23. These pores are generally filled with a matrix material as will be described subsequently as a membrane material and which extend over the exterior of tube 15 and in some instances, along the interior. Electrode wires 19 are wrapped tightly around tube 15 so as to imbed in any of the coating material and at least occasionally to make contact with the matrix media in the pore 23 itself. Because of the nature of the structure and method of manufacturing the product, it is not necessary that there be complete contact with all pores or even with most pores; occasional, random contact is adequate.

Figure 5:
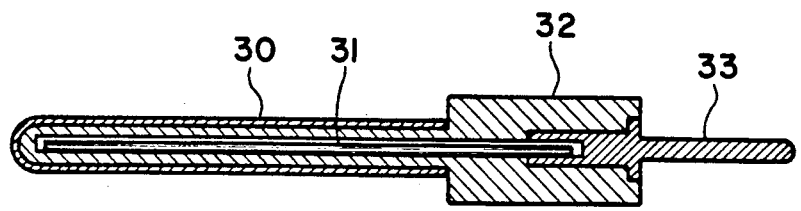
FIG. 5 is plan view in section of a dip type electrode in accordance with the present invention.

FIG. 5 is a plan view of a dip type electrode in which tube 30 is of the same general type described as 15 herein, except that it is closed at the end. Electrode 31 is preferrably a solid wire imbedded in the tube in contact with the pore filling matrix medium. It is possible, however, to have the electrode wire of the same diameter as the internal dimensions of the tube thereby completely filling the tube, so that the pores of tube 30 communicate through the matrix media in to direct contact with electrode wire 31. Electrode 31 is then fitted into appropriate fitting 32 with electrical connector 33 providing the external electrical contact for the dip electrode.

DETAILED DESCRIPTION OF THE EMBODIMENTS OF THE INVENTION

A porous tube of appropriate size is "soaked" or force coated with a solution containing the membrane material. The tube may be made of any suitably non-reactive porous material in which there is a communication of the pores through the tube wall. These pores should be generaly uniformly distributed over the active portion of the tube with the maximum pore size of about 100 microns. In the preferred embodiment, the tube is microporous, i.e., it has a maximum pore size of about 15 microns, and preferably of 10 microns. There is no lower limit on pore size other than the practical consideration of the pressures needed to force embrane material into the pores, as will be described in greater detail hereafter.

The tube material may be made from any suitably non-reactive tube material. A preferred material is micro-porous polytetrafluoroethylene. Examples of such tubing include GoreTex micro-porous PTFE tubing (W. L. Gore & Associates, Inc., Elkton, Md.), characterized as follows:

| Type | TA001 | TB001 |
|---|---|---|
| Inside diameter: | 0.039 inches. | 0.039 inches |
| Wall thickness: | 0.016 inches. | 0.016 inches |
| Maximum pore size: | 2.0 Microns | 3.5 Microns |
| Porosity | 50% | 70% |

Other tubes with different parameters are also available from the same manufacturer. The choice of the tube used and the specific porosity selected depends on the experimental conditions encountered in the system.

Another material that may be used is porous glass; an example of such a material is described in some detail in U.S. Pat. No. 3,607,702 to Haller. Of course, the Haller material must be formed into a generally tubular form to be useful for the purposes of the present invention. Still other materials are described in U.S. Pat. No. 3,445,365 to Russ. It would also be possible to use a porous polyvinylchloride or other porous polymeric material. The key in all of these selections, however, is to choose a material that will be essentially non-reactive and inert to the tests solutions for which it is to be used. In addition, it must be non-reactive with and essentially insoluble in the solvents and plasticizers of the membrane material used to impregnate the tube pores. The selection of the appropriate tube material is well within the ordinary skill of the art when considering the specific needs for a particular analytical system. With all of these, however, the microporous materials, as previously defined are preferred.

The membrane material can be any of the suitable membrane materials already known in the art. The membrane materials described in some detail in the aforementioned U.S. Pat. No. 4,233,136 and U.S. Pat. No. 4,314,895 are suitable for use herein with the provisos discussed above concerning the selection of tube material and solvent plasticizer material for compatibility and non-solvency.

A 2" length of the above PTFE tubing TA001 is soaked in a mixture consisting of 2 ml. 6% PVC solution (w/v) in tetrahydrofuran (THF), 2 ml. of Dioctyl Sebacate (Scientific Polymer Products) and 16 mg. of Valinomycin (Calbiochem). The tube slowly starts absorbing the reagent mixture. The soaking process can be followed by looking at the tube against bright light preferably with an ordinary magnifying glass or even naked eye. Over a period of 1 to 24 hours the whole tube becomes uniformly coated with the reagent mixture. After the tube is completely coated, it is taken out from the reagent mixture and the excess reagent drained out. A smooth, stiff rod whose diameter is slightly less than the inside diameter of the PTFE tube is then inserted through the soaked tube so that the rod comes out from the other open end of the tube. The tube is then allowed to dry on the rod at room temperature in a hood for 24 hours. During the drying process the volatile solvent THF evaporates leaving a coating of PVC, Valinomycin and the plasticizer in the pores and both the inside and outside walls of the tube. At this stage a 0.5 mm diameter silver wire is tightly wound around the outside of the coated tube (while its still on the rod). On top of the silver wire windings a second coat of the original reagent mixture is applied to the tube. This helps to bind the silver wire to the coated tube. Even without this coating over the windings the electrodes works fairly well. Ideally, the silver wire windings would cover only $\frac{1}{8}$ to $\frac{1}{4}$" length of the coated tube and are positioned preferably in the middle portion of the tube. After the second coating the tube is allowed to dry on the rod for about 4 hours at room temperature. After the second drying the tube is taken off the rod and allowed to dry at room temperature for about 24 hours. This drying also dries the inside of the tube. The smooth, stiff rod on which the tube was dried (when taken out) provides a smooth flow path for the analytical stream. The tube is now ready to be incorporated into an electrode holder for use as a flow-through electrode. The electrode holder with the tube installed in it is show in FIG. 3.

A second method for coating the porous tube with the reagent is the use of pressure to force the reagent into the pores of the tube. This is done as follows. A 6" length of the tubing is cut and one end of it is clamped tight with a hemostat. The reagent mixture is then introduced into the open end of the tube by means of a syringe and needle (the needle tightly fits the opening of the tube). Pressure is then applied on the syringe piston to force the reagent mixture into the porous tube. The pressure causes the reagent mixture to penetrate into the pores of the tube thereby giving a good coating. The tube is then taken out from the syringe and cut into desired length segments and soaked in the reagent mixture for uniform coating.

Force coating generally requires the use of a thinner reagent mixture (more THF solvent) to coat the tube. A second coating is generally necessary for a uniform coating of the reagent. Force coating generally reduces the soaking time by about 50%. But, coating of the tube by soaking seems to be more convenient and ideally suited for mass production.

After the coating over the silver wire winding is dry, the rod is taken out and the coated tube can be assembled into a proper electrode holder with inlet and outlet tubes for the flow-through electrode. The silver wire now serves as the internal reference electrode, eliminating the need for the clumsy Ag/AgCl (with KCl) reference electrode system.

This electrode has minimal drift, stabilizes fast, has long life, fast response and excellent wash characteristics. With proper work any of the liquid membrane electrodes can be made into this type of electrode.

EXAMPLE 1 THROUGH 6

The above made flow-through electrode was incorporated into a flow system using a peristaltic pump. An Ag/AgCl flow-through electrode with 0.1 M. KCl flowing through it was used as the reference electrode. The sample and reference streams meet after passing through the respective electrodes and then the combined stream goes to waste. Liquid junction is made close to the two electrodes. Orion model 801 PH meter was used to measure the potential readings in millivolts. Aqueous solutions of KCl were used as the standards.

Readings were taken with the liquid system flowing. The electrodes gave fast response and values stabilized in less than 5 seconds in most cases. At very low level i.e., $1 \times 10^{-6}$ M. it took longer to stabilize.

| Example | KCl,M/L. | Potential Reading, Millivolts | Millivolt Differences |
|---|---|---|---|
| 1. | $1 \times 10^{-6}$ | −212.4 | |
| | | | 15.8 |
| 2. | $1 \times 10^{-5}$ | −196.6 | |
| | | | 53.1 |
| 3. | $1 \times 10^{-4}$ | −143.5 | |
| | | | 59.5 |
| 4. | $1 \times 10^{-3}$ | −84.0 | |
| | | | 59.7 |
| 5. | $1 \times 10^{-2}$ | −24.3 | |
| | | | 59.9 |
| 6. | $1 \times 10^{-1}$ | +35.6 | |

As can be seen the above data shows good linearity.

The above flow-through electrodes generally stabilized in about 5 minutes when first installed in the flow-system and thereafter showed minimal drift over extended periods of time. Several electrodes were run continuously for more than 300 hours using aqueous KCl solutions as samples. The electrodes exhibit theoretical slopes through out the testing period. Even after 300 hours the response was fast and the drift was minimal. Due to time restraints, tests were terminated after 300 hours.

During the development of the above electrode a study was conducted to develop a correlation between plasticizer content of the membrane and the response, drift and the life of the electrode. It was found that the life of the electrode and the response characteristics are highly dependent on the plasticizer content of the membrane. Low plasticizer levels generally give shorter useful life. Also, in some cases the response of the electrode slows down. Use of higher plasticizer levels in the common PVC membrane electrode gives a soft and fragile membrane which is almost impossible to use. In the present invention it is possible to incorporate fairly high levels of plasticizer into the electrode matrix without harming the physical properties of the electrode too much. The increased levels of plasticizer generally extend the useful life of the electrode and also speed up the response time.

In the present invention it is also possible to further extend the life of the electrode by incorporating a reservior of the active ingredient mixture in the electrode holder such that the reservoir contacts the outside walls of the coated electrode tube. This, of course, is only possible with the direct solid state connection electrodes which do not have internal filling solution. Some of the liquid membrane electrodes e.g. chloride, carbonate etc., have active ingredients and/or plasticizers which have some solubility in the aqueous samples they come in contact with. This solubility of the ingredients causes them to be slowly washed out from the membrane. This shortens the useful life of the electrode and in some cases the selectivity of the electrode is also adversely affected. The present invention would minimize these problems by providing a reservoir of these ingredients which would replenish the membrane as they are used up thereby extending the useful life of the electrode considerably.

The reservior can be in various forms. For example, it may consist of an extra thick layer of the same reagent mixture which is used to coat the porous tube over the silver wire windings. Since the silver wire is tightly wound around the outside of the tube, the thickness of the membrane is for most part defined by the wall thickness of the tube. In the experiments it was found that even a thick layer of PVC mixture over the windings does not slow down the electrode response. It appears that the extra thick layer of the PVC-reagent mixture acts like a built in reservoir of the active ingredients (and the plasticizer) and replenishes the loss of any of these ingredients (within the membrane) either by solubility or by other means during usage or storage. In the case of a regular PVC membrane with internal filling solution, a too thick a membrane increases the impedance and also adversely affects the other performance characteristics of the electrode.

SOLID STATE DIP ELECTRODE

The present invention can also be used to make solid state dip electrodes. To make the dip electrodes, the coating procedure for the porous tubes is similar to the procedure described for coating the flow-through electrode tubes.

The tubes used for dip electrode are sealed at one end before applying the reagent mixture. After the tubes are thoroughly coated a tight fitting silver rod is inserted from the open end of the tube and pushed in till it touches the sealed end of the tube. Before inserting into the tube the silver rod is first coated (by dipping) with the PVC-reagent mixture. The tube with the rod inside is then allowed to dry at room temperature for 24 hours. After drying an electrical lead is connected to the exposed portion of the silver rod. The whole electrode is then sealed in a second tube exposing only the tip and a small portion of the coated tube. This sealing prevents any of the test solution from coming in direct contact with the silver rod. The attached electrical lead provides connection to the electrometer. The performance characteristics of the dip electrode are similar to the above described flow-through electrodes. Other uses of the technique.

1. It should be possible to immobilize the enzymes in the porous tubes for use in electrodes and as enzyme reactor coils.

2. It should be possible to precipatate water insoluble or low water soluble salts or mixtures of these salts, e.g., silver chloride, silver sulfide, lanthanum flouride etc., in the matrix of the porous tubes (by suitable means) and then use the tubes as flow-through electrodes for the appropriate ions.

3. Metallic contacts other than silver work well. Pt. Au, Cu, etc.

4. Wide variations in the PVC, Valimonycin and plasticizer levels are possible.

From the foregoing it may seen that the present invention provides a number of new developments which can be utilized independently of each other but which, at the same time, interact to provide a superior and preferred electrode assembly. Thus for example, the porous tubing impregnated with the membrane material may be utilized essentially identically to the tubing shown in U.S. Pat. No. 4,233,136 to Spazani et al, to provide an electrode assembly that is more stable and has a longer operating life than the Spazani electrode assembly, all other aspects being identical. Further, the Spazani electrode assembly can be used identically in the manner described by Spazani et al except that the Spazani reference electrode and reference liquid contained within the electrode assembly are replaced with a direct contact metal wire in direct electrical contact with the membrane shown by Spazani to provide a further improved electrode assembly. In this case, the reference liquid of Spazani can be replaced by a plasticizer/active ingredient mixture to thereby provide not only a more reliable system but also a longer-lived system which can operate for periods of time long beyond that contemplated by Spazani et al. In that modification, the electrode wire is preferably held in place against the membrane material by a further coating of membrane material. Finally, as should be recognized, the ultimate and most preferred electrode assembly of the present invention is that exemplified in FIGS. 3 and 4 of the present invention, in which the electrode wire is in direct contact with pores of the porous or microporous tubing and in which the pores are filled with the membrane material and preferably where the wire is sealed to the tubing with an additional coating of the membrane material. When this particular electrode assembly is introduced into a system as shown in FIG. 2, with the fluid system contained in the electrode container consisting of a mixture of the plasticizer/active ingredient mixture, a very long-lived stable electrode assembly is obtained which can give long and reliable service without continual replacement. As also noted, the present invention provides a very superior and long-lived dip electrode significantly different than those experienced in the past.

Further study of the solid state connection to the microporous tube showed that:

1. A thick coat of the reagent mixture over the Ag wire windings and the outer layer of the tube helps to minimize noise pick up and also minimize drift, thereby giving a more stable and reproducible electrode. The thick coat also acts as a reservoir of the active ingredients, thereby extending the life of the electrode. This heavy coat also gives a more reproducible offset potential, i.e. the potential generated by each electrode from a large batch of electrodes at a given level of concentration of the sample against a reference electrode would be very close to each other. This is highly desirable. Preferably, the coat should be at least one millimeter and, more preferably, two millimeters greater than the wire thickness.

2. With the microporous impregnated tubes and solid state connection, metal nipples can be used for both inlet and outlet of the sample stream. These are shown in the FIGS. 1, 2 and 3, as items 13 and 14. The electrode tube is directly connected by these metal nipples to the lines carrying the samples. This has never been possible before, particularly with liquid or gel filled electrodes due to the tendency to short circuit. That is not a problem with the present invention. The advantages of metal nipples, provided the metal is nonreactive with the sample streams, are well known. They are more durable and are far more easily made in the small diameters necessary for this technology. Thus, in the preferred embodiment of the invention, metal nipples are used in direct contact with electrode membrane tube and also the sample stream. The membrane tube is a Teflon tube which has hydrophobic characteristics which impede the ingress of the charged species into the membrane, thereby giving better selectivity and improved drift characteristics.

The preferred embodiment of the potassium electrode membrane utilizes the reagent mixture comprising:

| Valinomycin | 40 mg. |
| Di-(2-Ethylhexyl) Sebacate [Dioctyl Sebacate] | 4.5 g. |
| 6% PVC in Tetrahydrofuran (v/w) | 7.3 g. |
| Tetrahydrofuran | 4.0 g. |

The advantages and improvements which can be achieved by the use of microporous tube electrode technology to ion-selective electrodesis shown dramatically by its application to carbonate analysis. W. J. Scott, et al, described in detail the making, use and limitations of an ion-selective membrane electrode for the measurement of total carbon dioxide (as carbonate) in human sera samples. Although this carbonate electrode is functional and useful for carbonate measurement, it has several drawbacks and serious interference problems with various drugs and/or their breakdown products in human sera. Some large anions also interfere. To minimize these interferences, Scott, et al, recommend the use of an enhancer in the membrane formulation and a mercury complexone in the buffer medium used for diluting the sample. Mercury salts are poisonous and their use in the buffer reagent causes serious handling and disposal problems for the waste reagents and, as such, is not desirable. Also, the life of this electrode is limited. The membrane has to be replaced at least once a week and in some cases more often. Even during this one week period the interferences increase with usage and aging of the membrane.

The new carbonate electrode developed using the microporous tube electrode technology has been able to overcome most of the problems and drawbacks described above. The interferences from drugs (and/or their breakdown products) and some large anions have been reduced to such an extent that the use of enhancer such as 1-phenyldecane in the electrode coating formulation is no longer needed. The teflon microporous tube itself provides the necessary hydrophobic characteristics which impede the ingress of the charged species into the membrane tube. This improves the drift characteristics and reduces the interferences. Further, there is no need for the use of mercury salt containing complexone reagent in the buffer medium. This is highly desirable. Microporous tube electrode technology allows the use of coating mixture with high levels of critical ingredients and still gives firm and useable electrodes. With regular membrane casting, the membrane would come out soft (or as gel) and would not be usable as an electrode. With higher level loadings of the various critical ingredients the useful life of the electrode has been extended considerably, frequently up to four times greater. It should be clearly pointed out that not only higher levels of the active ingredients in the reagent mixture but also a critical balance of these ingredient levels to each other is needed to get the desired selectivity and extended life out of the carbonate electrode. In the carbonate electrode, the proportion of tetraoctyl ammonium bromide to p-decyl-alpha-alpha-alpha-trifluoroacetophenone is critical for good selectivity and extended life. Too much or too little of either one in the reagent coating mixture gives an electrode which has poor selectivity and short life. This aspect of the formulation has not been reported in literature before. As an illustration, a typical reagent mixture used to impregnate the microporous tube contains the following range of ingredients, with a preferred formulation in parentheses:

1. p-Decyl-alpha, alpha, alpha-Trifluoroacetophenone: 0.4 to 0.8 g.; (0.6).
2. Tetraoctyl ammonium bromide: 0.2 to 0.4 g.; (0.3).
3. Di-(2-ethylhexyl) Adipate: 2.5 to 4.0 g. (2.5)
4. 6% solution of polyvinyl chloride high molecular weight in Tetrahydrofuran (w/v): 4.0 to 6.0 g.; (4.0)
PVC=polyvinyl chloride high molecular weight.
THF=Tetrahydrofuran.

The ingredients are mixed together to get a uniform mixture. The microporous tube coating/impregnating procedure is the same as described for the potassium electrode. As is generally known, the higher molecular weight film forming PVC polymers are preferred to the lower molecular weight materials.

The carbonate electrode made according to the above procedure gives a Nernst slope of 20-28 mv per tenfold change in carbonate level encountered in the sample. The sample is diluted (generally 10 to 14-fold) with a buffer of pH of approximately 8.6 for the measurement. Since the carbonate ion is divalent, the Nernst slope in this case theoretically is only one-half of the slope obtained with monovalent cation electrode like potassium.

The carbonate electrode described in the literature goes into a "shock" when it is exposed to an interfering substance in the sample. This causes not only the sample containing the interfering substance to give erroneous reading, but in some cases the following "normal" sample values are also invalidated. The improved carbonate electrode using the microporous tube minimizes these erroneous results.

While the invention has been further illustrated and described in specific manner, it is not intended to be limited to detail shown since various modifications and structural changes may be made without departing in any way from the spirit of the present invention.

The potassium electrode is a monovalent cation electrode and the carbonate electrode is a divalent anion electrode. The application of the microporous teflon tube coating/impregnating technology to make ion-selective electrode membrane tubes for such diverse species clearly demonstrates the wide applicability of this technology to varying species of ion-selective electrodes. The same type of technology can be used to make electrodes for calcium, chloride, lithium, magnesium, et cetera, ion-selective electrodes with marked improvement and desirable performance characteristics as shown with the above two examples. Novelty is not claimed in the choice of specific matrix materials used for the membrane described herein, but is directed primarily to the structures involving direct electrode contact and/or involving the use of a porous flow-through or other tubular material and the impregnation of those pores with the membrane material. It is to be noted that the solvents used to load the matrix material into the pores is not a solvent for the tubular materials since this would cause a collapse of the relatively small pores particularly in the case of the microporous products.

Other embodiments of this invention will occur to those skilled in the art when viewing the disclosure examples, appended drawings and claims.

What is claimed is:

1. A dip electrode assembly of the ion-selective type used for the analytical determination of ion concentrations in a solution and comprising, in combination:
   (a) A tube having a closed end and an open end and adapted for emersion of said closed end portion of said tube into a solution to be analyzed, said tube comprising a porous material having pores generally uniformly distributed there through, said pores communicating between the inside and the exterior of said tube, the maximum pore size of the pores in said tube being 100 microns in diameter;
   (b) An electrode extending through said open end of said tube and adapted to be connected to an electrometer;
   (c) Means for sealing said electrode to said tube adapted to permit connection of said electrode to an electrometer; and
   (d) A membrane matrix material comprising an organic plastic material comprising a nonvolatile solvent plasticizer and an ion-active material dissolved in said plasticizer, said plasticizer being essentially nonreactive with and a nonsolvent for said tube, said membrane matrix material impregnating the pores of said tube and directly contacting said electrode.

2. A dip electrode in accordance with claim 1 in which said tube is microporous, having a maximum pore size of about 15 microns in diameter.

3. A dip electrode assembly in accordance with claim 2 in which said tube is polytetrafluoroethylene and said pore size is less than 10 microns in diameter.

* * * * *